US007422593B2

(12) United States Patent
Cresina et al.

(10) Patent No.: US 7,422,593 B2
(45) Date of Patent: Sep. 9, 2008

(54) EXTERNAL FIXATION SYSTEM

(75) Inventors: Jeffery Cresina, Middlesex, NJ (US);
Takkwong R Leung, Piscataway, NJ (US); Stephen Walulik, Phillipsburg, NJ (US); Stephen Conti, Sewickley, PA (US)

(73) Assignee: EBI, L.P., Parsippany, NJ (US)

( * ) Notice: Subject to any disclaimer, the term of this patent is extended or adjusted under 35 U.S.C. 154(b) by 217 days.

(21) Appl. No.: 11/297,745

(22) Filed: Dec. 8, 2005

(65) Prior Publication Data

US 2007/0161983 A1 Jul. 12, 2007

(51) Int. Cl.
*A61B 17/00* (2006.01)
*A61F 4/00* (2006.01)
(52) U.S. Cl. .............................. 606/54; 606/57; 606/59
(58) Field of Classification Search .................. 606/54, 606/55, 56, 57, 58, 59
See application file for complete search history.

(56) References Cited

U.S. PATENT DOCUMENTS

| 2,393,831 | A | | 1/1946 | Stader | |
|---|---|---|---|---|---|
| 4,308,863 | A | | 1/1982 | Fischer | |
| 4,338,927 | A | | 7/1982 | Volkov et al. | |
| 4,365,624 | A | | 12/1982 | Jaquet | |
| 4,450,834 | A | | 5/1984 | Fischer | |
| 4,456,004 | A | * | 6/1984 | Kenny | 606/57 |
| 4,483,334 | A | | 11/1984 | Murray | |
| 4,535,763 | A | * | 8/1985 | Jaquet | 606/56 |
| 4,768,524 | A | | 9/1988 | Hardy | |
| 4,784,125 | A | * | 11/1988 | Monticelli et al. | 606/56 |
| 4,890,631 | A | | 1/1990 | Hardy | |
| 4,998,935 | A | | 3/1991 | Pennig | |
| 5,087,258 | A | * | 2/1992 | Schewior | 606/56 |
| 5,095,919 | A | * | 3/1992 | Monticelli et al. | 606/56 |
| 5,144,943 | A | | 9/1992 | Luttrell et al. | |
| 5,443,464 | A | | 8/1995 | Russell et al. | |
| 5,454,810 | A | | 10/1995 | Pohl et al. | |
| 5,458,599 | A | | 10/1995 | Adobbati | |
| 5,797,908 | A | | 8/1998 | Meyers et al. | |
| 5,997,537 | A | * | 12/1999 | Walulik | 606/56 |
| 6,030,386 | A | | 2/2000 | Taylor et al. | |
| 6,328,737 | B1 | | 12/2001 | Moorcroft et al. | |
| 6,342,054 | B1 | | 1/2002 | Mata | |
| 2002/0042613 | A1 | | 4/2002 | Mata | |
| 2003/0149429 | A1 | | 8/2003 | Ferrante et al. | |
| 2005/0059968 | A1 | | 3/2005 | Grant et al. | |

* cited by examiner

*Primary Examiner*—Pedro Philogene
(74) *Attorney, Agent, or Firm*—Harness, Dickey & Pierce, PLC

(57) ABSTRACT

An external fixation system for a bone and associated method. The fixation system includes a proximal frame defining a continuous proximal boundary, a distal frame defining a continuous distal boundary, and at least one frame connector configured for interconnecting the proximal and distal frames at any position along at least one of the proximal and distal boundaries.

15 Claims, 12 Drawing Sheets

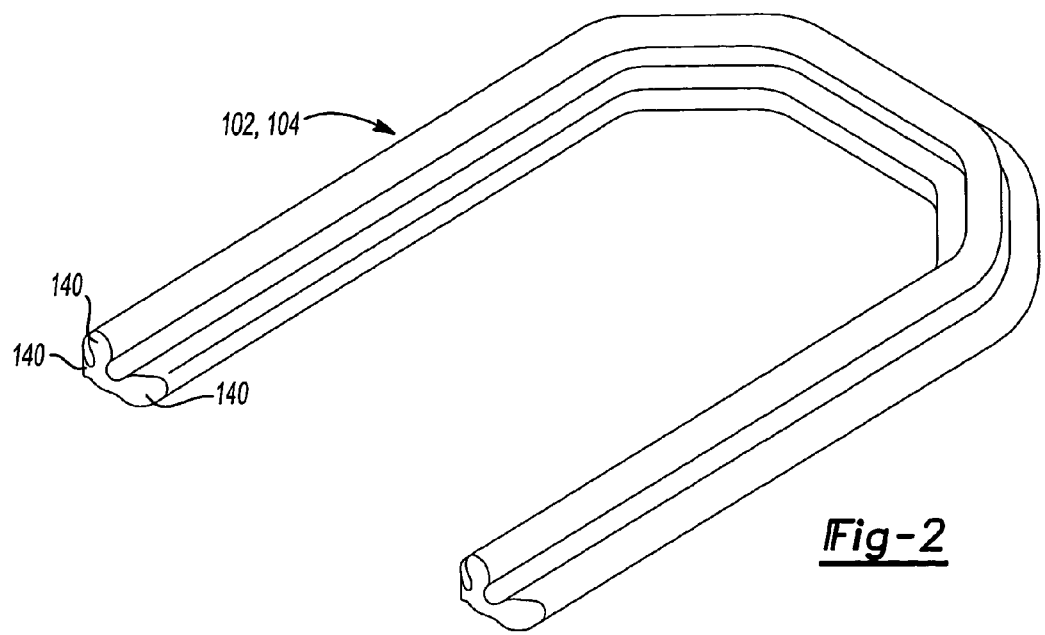
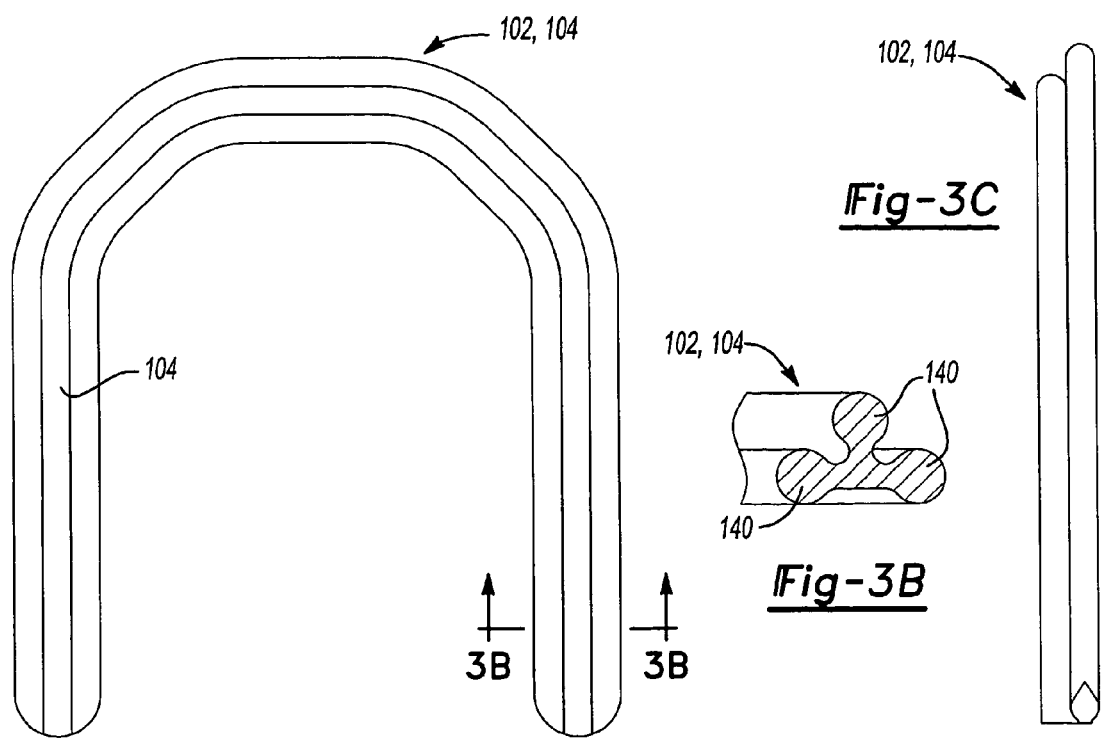

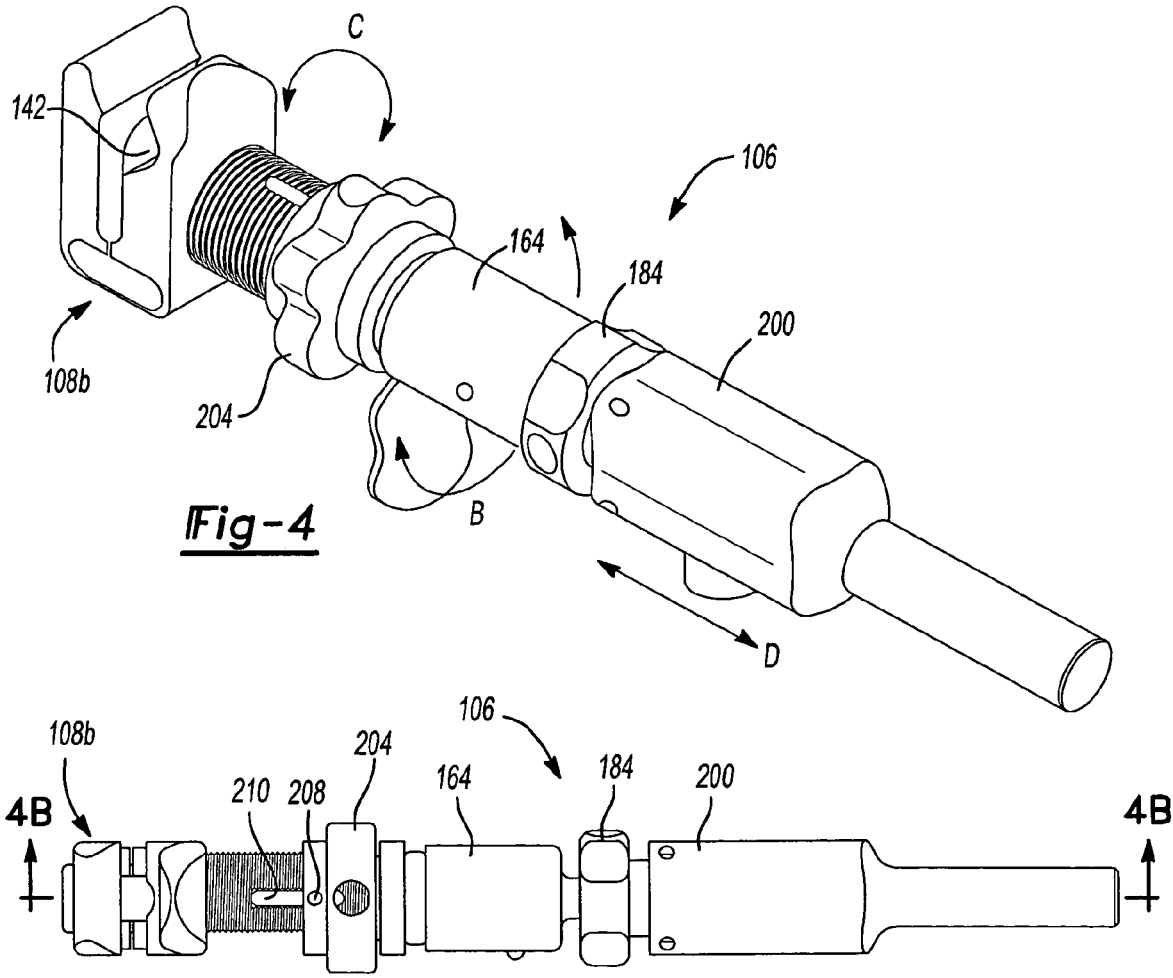
*Fig-4*
*Fig-4A*
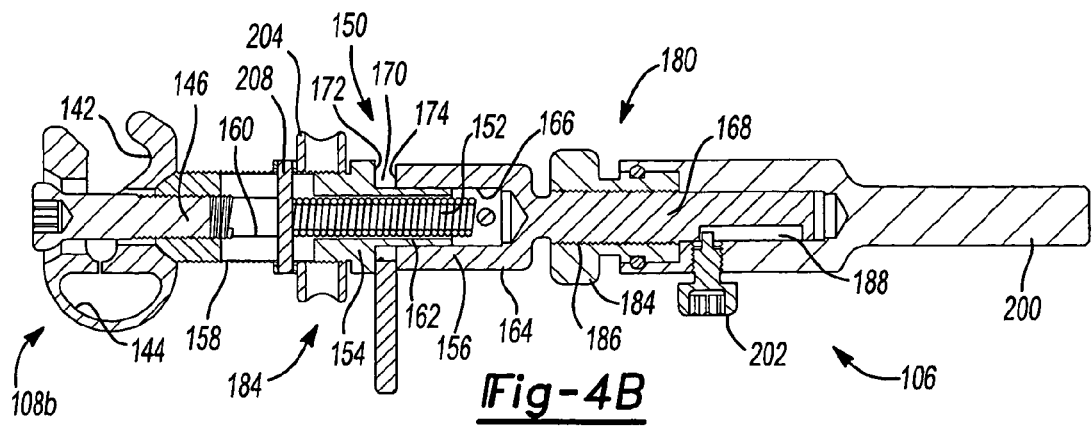
*Fig-4B*

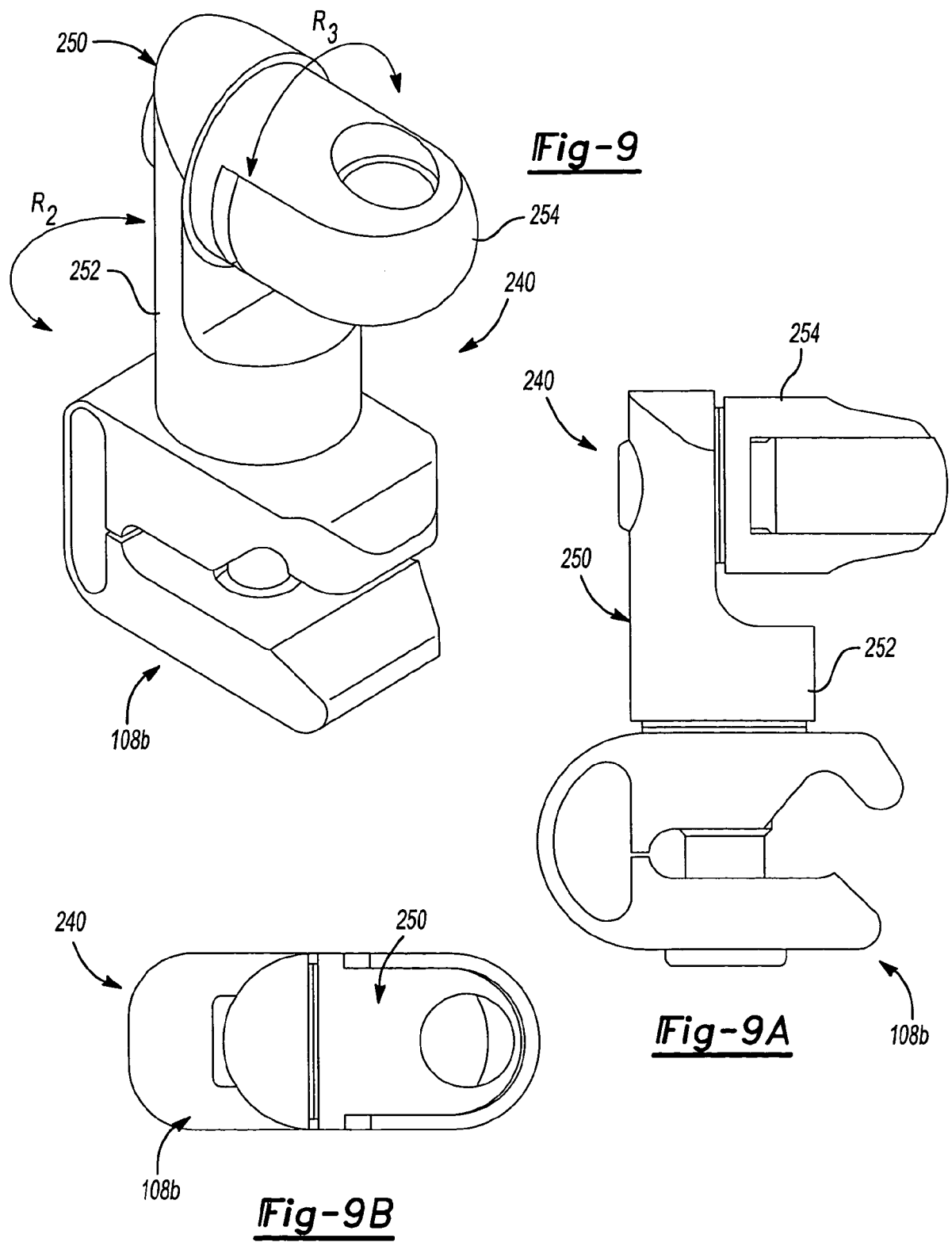

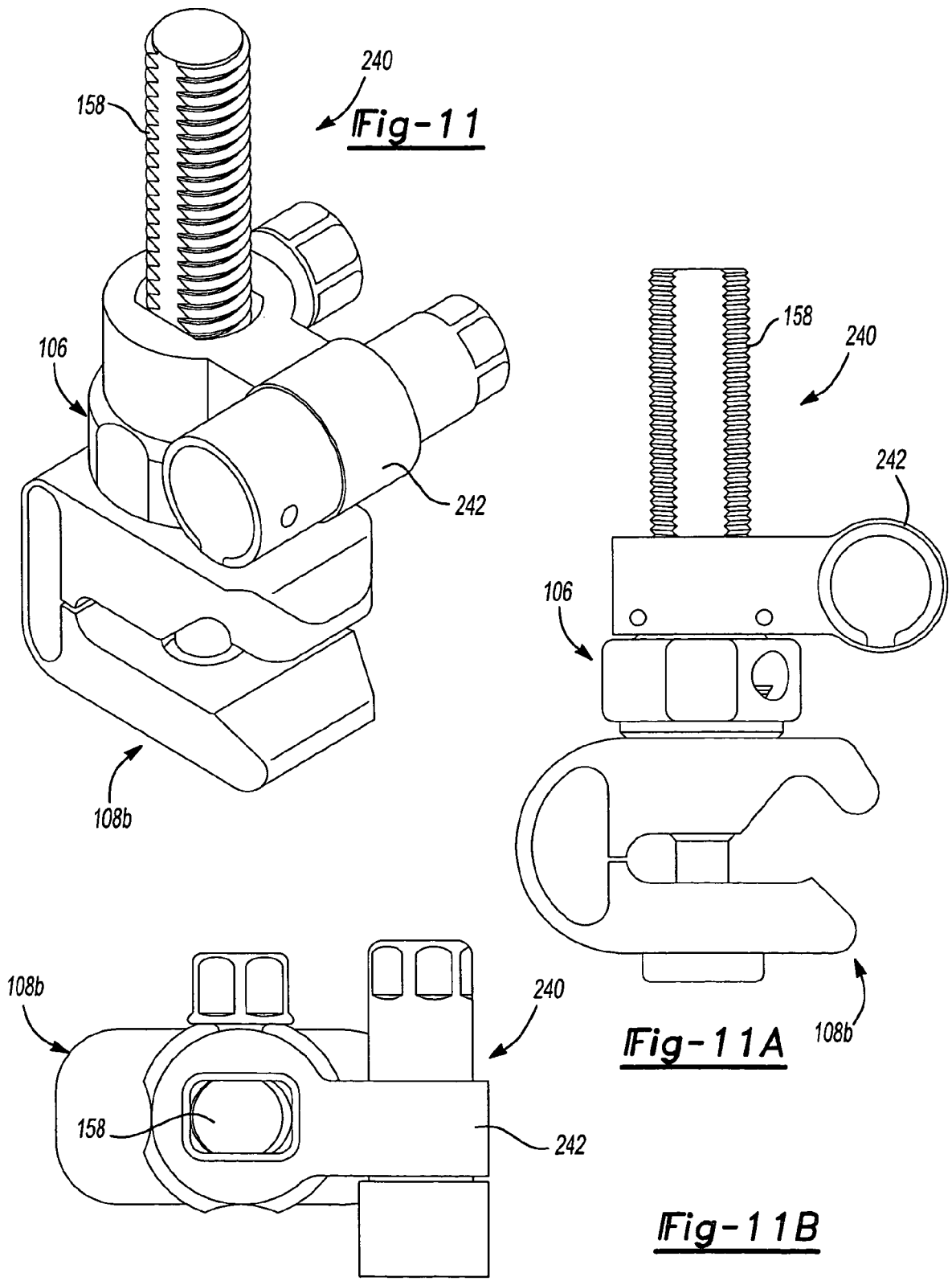

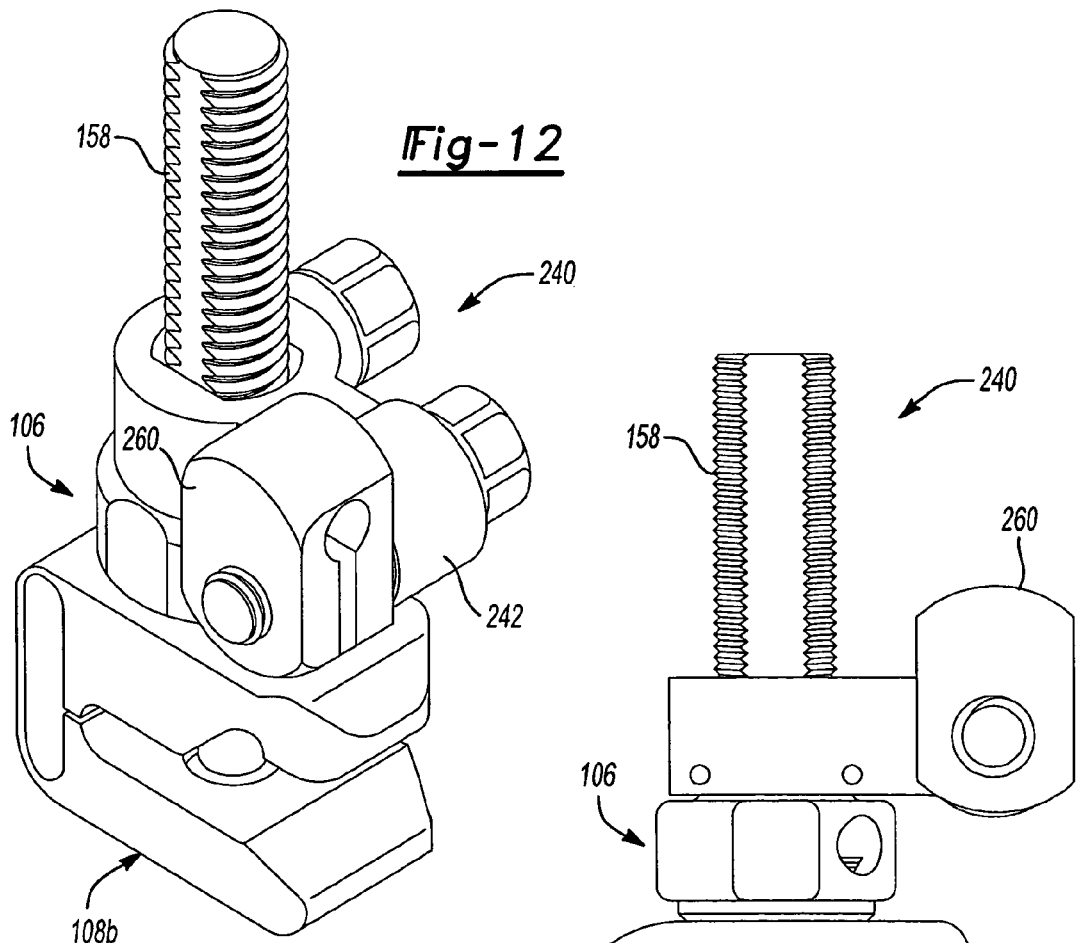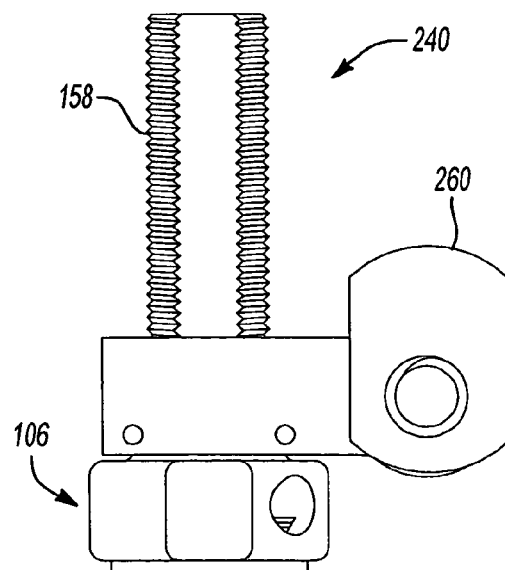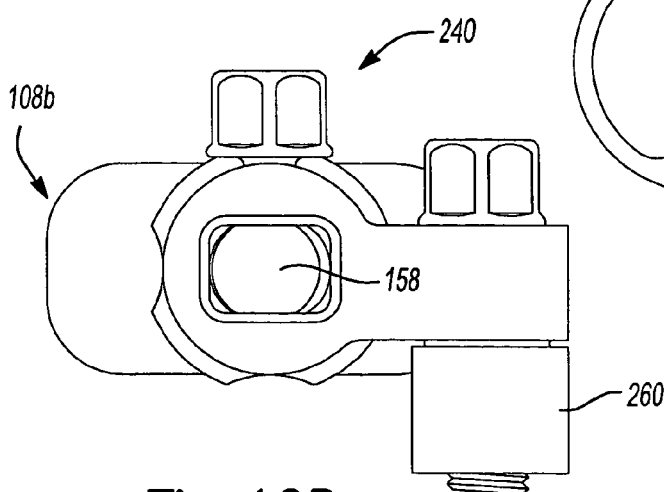

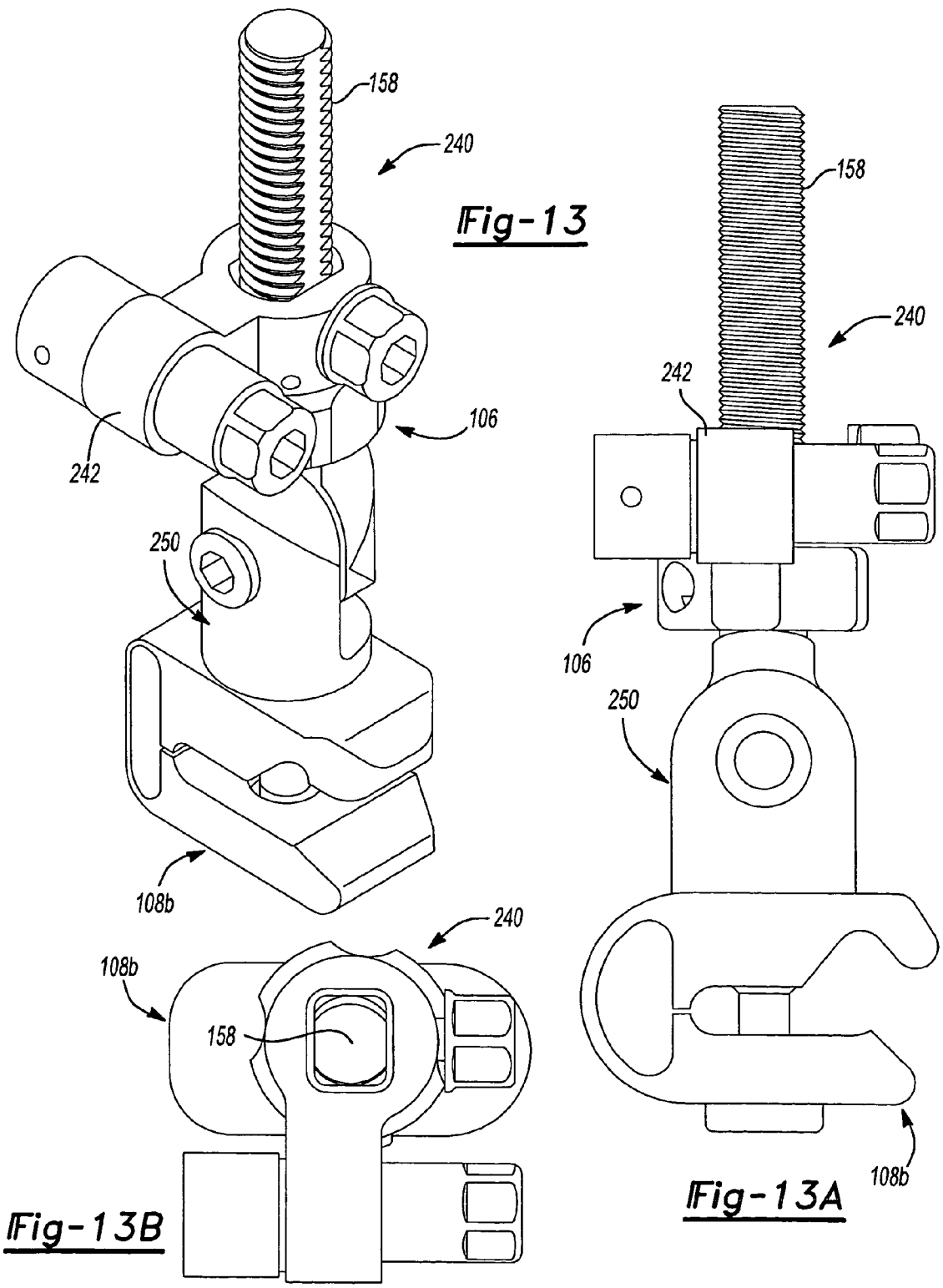

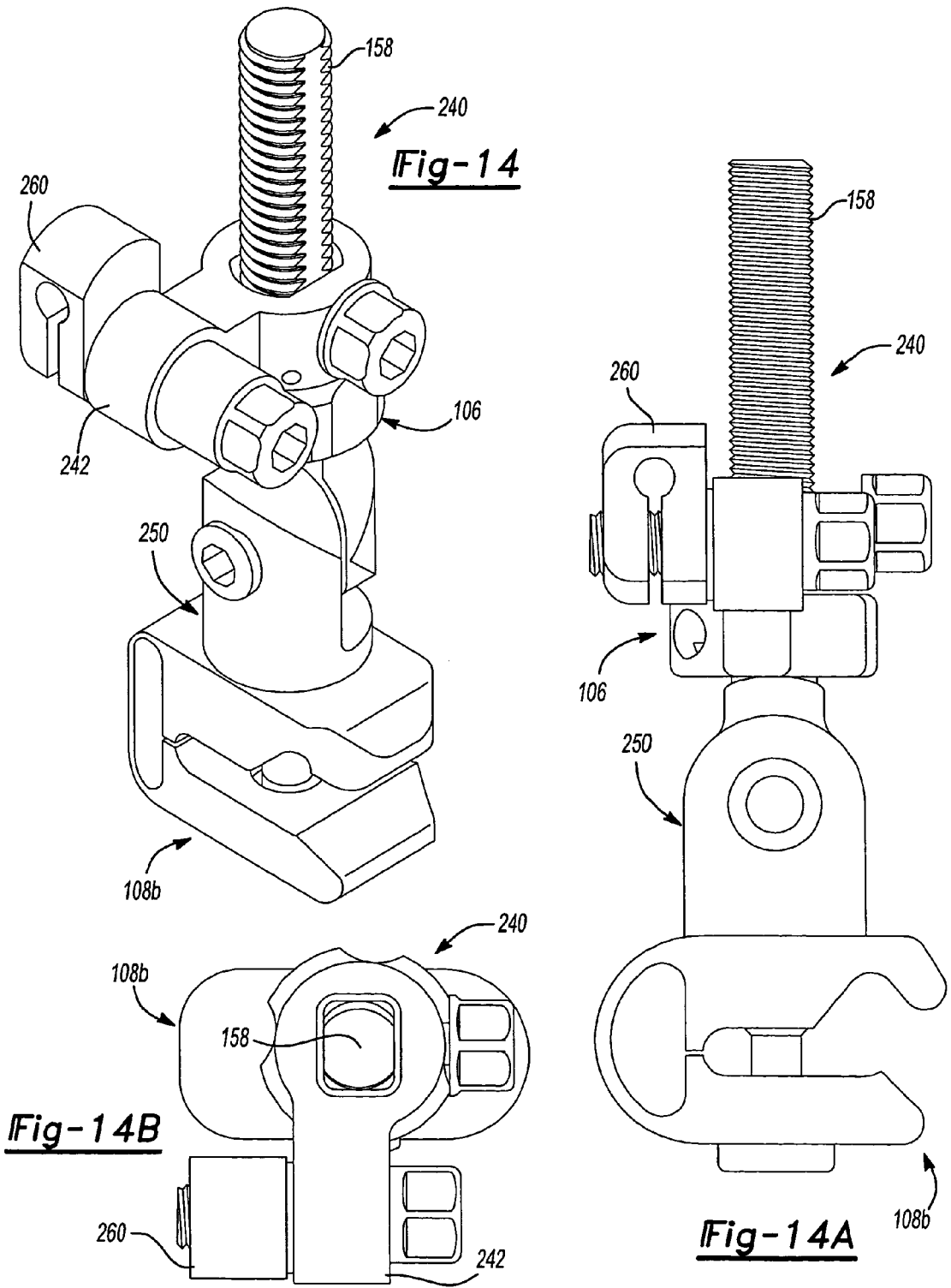

EXTERNAL FIXATION SYSTEM

Various external fixation systems are available for addressing fractures of various bones, including the distal tibia and the foot, and for arthrodesis, deformity correction or other foot management. Some of the existing fixation systems allow radiographic examination of the fracture site. In some systems, telescopic rod connectors attached at predetermined locations provide load across the fracture site.

Although the existing external fixation systems can be satisfactory for their intended purposes, there is still a need for external fixation systems that are versatile, easily customizable, and able to address distal tibia and foot fracture and fusion conditions.

SUMMARY

The present teachings provide an external fixation system for a bone, and associated methods. The fixation system includes a proximal frame defining a continuous proximal boundary, a distal frame defining a continuous distal boundary, and at least one frame connector configured for interconnecting the proximal and distal frames at any position along at least one of the proximal and distal boundaries.

The present teachings also provide an external fixation system for a bone that includes a proximal frame interconnected to a distal frame by at least one frame connector structurally configured for transmitting a compressive force of constant magnitude to the bone during non load-bearing use, and further structurally configured for automatically adjusting the magnitude of the compressive force to the bone during load-bearing use.

The present teachings provide a method for external fixation of a bone. The method includes attaching proximal and distal frames to the bone, interconnecting the proximal and distal frames at any position thereon, and transmitting an adjustable compressive force magnitude to the bone.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2 is a perspective view of a frame for external fixation system according to the present teachings;

FIG. 3A is a plan view of a frame for external fixation system according to the present teachings;

FIG. 3B is a cross-sectional view of the frame of FIG. 3A taken along axis 3B-3B;

FIG. 3C is a side view of the frame of FIG. 3A;

FIG. 4 is a perspective view of a frame connector for an external fixation system according to the present teachings;

FIG. 4A is a plan view of the frame connector of FIG. 4;

FIG. 4B is a sectional view of the frame connector of FIG. 4 taken along axis 4B-4B;

FIGS. 9, 9A, and 9B are perspective, side, and plan views, respectively, of a clamping assembly according to the present teachings;

FIGS. 11, 11A, and 11B are perspective, side and plan views, respectively, of a clamping assembly according to the present teachings;

FIGS. 12, 12A, and 12B are perspective, side, and plan views, respectively, of a clamping assembly according to the present teachings;

FIGS. 13, 13A, and 13B are perspective, side, and plan views, respectively, of a clamping assembly according to the present teachings; and FIGS. 14, 14A, and 14B are perspective, side, and plan views, respectively, of a clamping assembly according to the present teachings.

DESCRIPTION OF EXEMPLARY EMBODIMENTS

Figure 1:
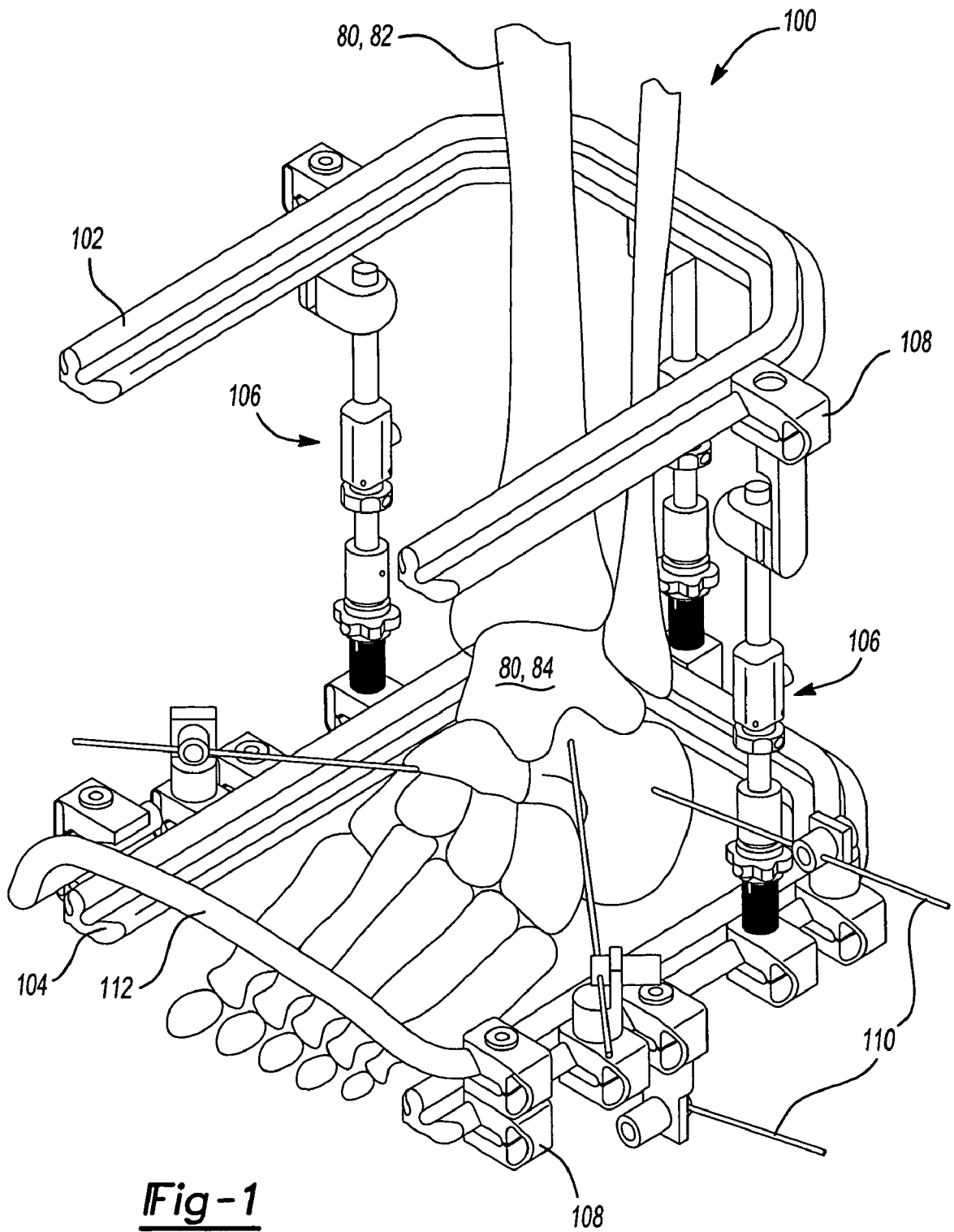
FIG. 1 is a perspective view of an external fixation system according to the present teachings, the external fixation system operatively attached to a foot.

The following description is merely exemplary in nature and is in no way intended to limit the invention, its application, or uses. For example, although the present teachings are illustrated for applications addressing fractures and/or deformities in the distal tibia and or various parts of the foot, the present teachings can be used for external fixation of other bones Referring to FIG. 1, an exemplary external fixation system 100 according to the present teachings is illustrated in an environmental view for fixation of various bones or bone portions 80, such as the distal tibia 82 and/or various foot bones 84. The fixation system 100 can include a proximal frame 102 and a distal frame 104, which can be positioned on opposite sides of a fracture/fusion site of the bone 80. The proximal and distal frames 102, 104 are connected to each other by one or more frame connectors 106, which can be selected from various configurations. Various clamps 108 can be used with the frame connectors 106 or independently of the frame connectors 106 for attaching bone pins or wires 110, and/or rods, bars, or other fixation devices 112, as desirable for a particular fixation. The proximal and distal frames 102, 104, the frame connectors 106, the clamps 108, or portions thereof, can be radiographically translucent, such that the fixation system 100, when installed, can allow viewing of a fracture/fusion site of the bone 80 on X-ray film. The radiolucent components or portions thereof can be formed of, for example, carbon, composite, carbon fiber, or other radiolucent materials.

Referring to FIGS. 2, and 3A-3C, various views of the proximal/distal frames 102, 104 are illustrated. It should be appreciated that although identical illustrations are used to show the proximal and distal frames 102, 104, differently sized or shaped frames can also be used. At least one of the proximal and distal frames 102, 104 can have a tri-lobe cross-section defined by three continuous attachment lobes 140 oriented in a three-dimensional configuration, which can be symmetric or non-symmetric. The attachment lobes 140 provide three separate and spaced-apart continuous attachment surfaces, such that the corresponding proximal or distal frame 102, 104 defines a continuous boundary, at any position of which a frame connector 106 or a frame clamp 108b can be attached. Each lobe 140 can have a substantially curved cross-section, such as a portion of circle or other curve portion. Each of the proximal and distal frames 102, 104 and the associated attachment lobes 140 can be generally U-shaped, although other closed- or open loop shapes can be used.

Referring to FIGS. 4, 4A, and 4B, an exemplary frame connector 106 is illustrated in further detail. The frame connector 106 can be coupled to the proximal and distal frames 102, 104 using frame clamps 108b at each end of the frame connector 106 (one frame clamp 108b is shown in FIGS. 4, 4A, and 4B). The frame clamp 108b includes a jaw opening 142 which can be configured for snap-on clamping on any of the attachment lobes 140 at any position thereon. The frame clamp 108b can also include another opening 144, for receiving any one of various rods, connectors, couplers and adapters for coupling with other fixation components or devices. The opening 144 can also be shaped for constraining rotation having, for example, a D shape. The frame clamp 108b can be coupled to the frame connector 108b using a fastener 146.

With continued reference to FIGS. 4, 4A and 4B, the frame connector 106 can include a compliant mechanism 150 configured for transmitting adjustable compressive force to the fracture/fusion site of the bone 80 between the proximal and distal frames 102, 104. The compliant mechanism 150 can include a biasing element 152, such as, for example, a spring, coupled between first and second telescopically inter-engaged connector members 154, 156. The first connector member 154 can be, for example, a cannulated screw defining a through bore 160, and having a threaded portion 158 and a stem 162. The second connector member 156 can include a sleeve 164 defining a bore 166, and a rod or bar 168 attached to the sleeve 164. The stem 162 of the first connector member 154 can be configured to be received in the bore 166 of the sleeve 164 such that the biasing element 152 extends between the first and second connector members 154, 156. The first and second connector members 154, 156 can move in a telescopic fashion axially relative to one another, such that a gap 170 of variable magnitude (opening width) can be formed between corresponding abutment surfaces 172, 174. When the gap 170 is substantially closed, the biasing element 152 is in an undeformed/non-activated configuration and does not transmit any force between the first and second connector members 154, 156. When the gap 170 is opened, the biasing element 152 is in a deformed/activated configuration and can transmit a force between the first and second connector members 154, 156. The magnitude of the transmitted force can be controlled by initiating and selecting the magnitude of the gap 170, as discussed below.

The frame connector 106 can include an actuation mechanism 180 for activating the biasing member, and a selector mechanism 182 for selecting the magnitude of the compressive force. In the exemplary illustration of FIG. 4B, the actuation mechanism 180 can include an activation knob 184 having a bore 186 threadably coupled to the bar 168 therethrough and secured on an extension member 200. A portion of the bar 168 that extends out of bore 186 of the activation knob 184 is received in a bore 188 of the extension member 200. Rotating the activation knob 184 in one direction opens the gap 170 by a small amount and activates the biasing member 152. A set screw 202 can be inserted transversely to the bore 188 for engaging the bar 168 and securing the bar 168 relative to the extension member 200. The bar 168, the activation knob 184, the set screw 202 and the extension member 200 define a compression/distraction connector similar to the one discussed below in reference to FIGS. 5-7.

The selector mechanism 182 can include a force-selector knob 204 threadably connected to the threaded portion 158 of the first connector member 154. Rotating the selector knob 204 in one direction causes a pin 208 to move along a slot 210 formed on the threaded portion 158 of the first connector member 154. This motion causes the gap 170 to increase in magnitude, stretches the biasing member 152, and increases the force transmitted by the biasing member 152. A removable spacer 206 can be used for gap and/or compressive force measuring purposes, with the width of the spacer 206 serving as a unit, such that, for example, an opening of the gap 170 equal in magnitude to the width of the spacer 206 can correspond to a predetermined increment of compressive force. Accordingly, the frame connector 106 can provide variable and selectable compression to the bone 80 across the fracture/fusion site. Referring to FIG. 4, the frame connector 106 can also provide telescopic/axial adjustability, as indicated by bi-directional arrow "D", rotational adjustability as indicated by curved arrow "B", and rotational adjustability at the frame clamp 108b for connection with the proximal and distal frames 102, 104.

Using the frame connector 106, a constant compressive force of a desired magnitude can be transmitted to the fracture/fusion site using the actuation and selector knobs 184, 204, as discussed above, under non-load bearing use. During load-bearing use, the frame connector 106 can automatically adjust the magnitude of the compressive force across the fracture/fusion site to the amount recommended by the surgeon. Automatic adjustability can be effected by the interaction between the force applied by the patient during load-bearing use and the compliant mechanism 150. More specifically, the magnitude/width of the gap 170 can be reduced by the force applied by the patient, as that force acts to reduce the expansion of the biasing member 152. As the magnitude of the gap 170 is gradually reduced during load-bearing use from an initial magnitude selected for non-load bearing use, the compressive force transmitted to the fracture/fusion site is gradually reduced, as discussed above.

Figure 5:
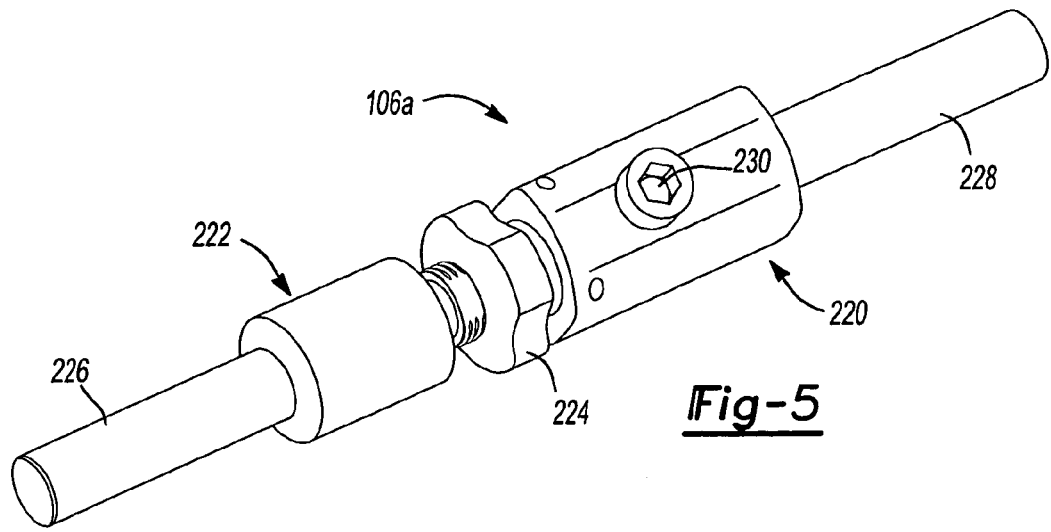
FIG. 5 is a perspective view of a contraction/distraction connector according to the present teachings.
Figure 6:
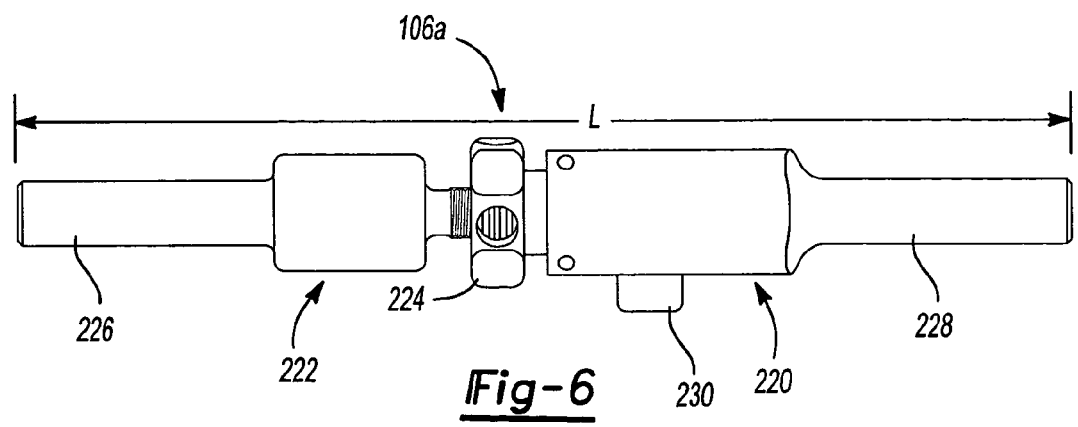
FIG. 6 is a plan view of a contraction/distraction connector according to the present teachings.
Figure 7:
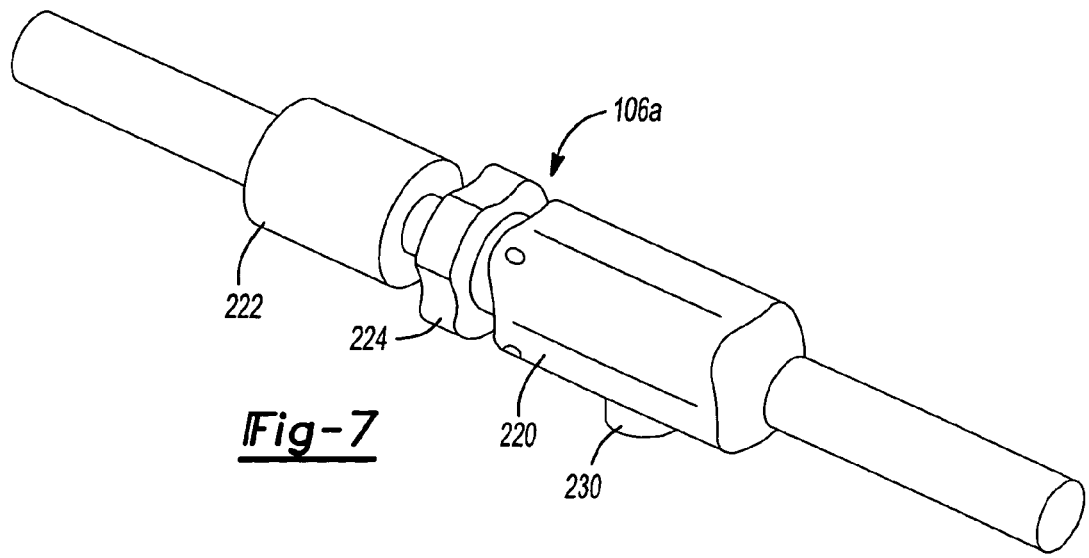
FIG. 7 a perspective view of a contraction/distraction connector according to the present teachings.

Referring to FIGS. 5-7, a compression/distraction connector 106a that can be used with the clamp 108 at one or both ends is illustrated. The compression/distraction connector 106a can include first and second members 220, 222 coupled to each other for axial/telescopic motion, which can be controlled by a knob 224, as illustrated in FIG. 6. The knob 224 can be similar in construction to the activation knob 184 shown in FIG. 4B. The knob 224 can be attached to the first member 220, and can be internally threadably connected to the second member 224. Rotating the knob 224 clockwise or counterclockwise causes relative motion between the first and second members 220, 222, such that the overall length "L" of the compression/distraction connector 106a decreases or increases causing contraction/distraction between the structures attached to the ends 222, 226 of the contraction/distraction connector 106a. A set screw 230 can be used to maintain a desired magnitude of the length L, as described in connection with the similarly-functioning set screw 202 in reference to FIG. 4B.

Referring to FIGS. 8-14, exemplary clamping assemblies 240 are illustrated for use with the external fixation system 100 to accommodate various fixation requirements, geometries and/or conditions. Generally, the clamping assemblies 240 can provide multiple rotational and translational degrees of freedom and can be used to interconnect various components of the external fixation system 100, such as the proximal and distal frames 102, 104, the frame connectors 106, the contraction/distraction connectors 106a, various bone screws, or other pins/wires 110, and various rods, bars, shafts or other fixation devices 112, as illustrated in FIG. 1.

Figure 8:
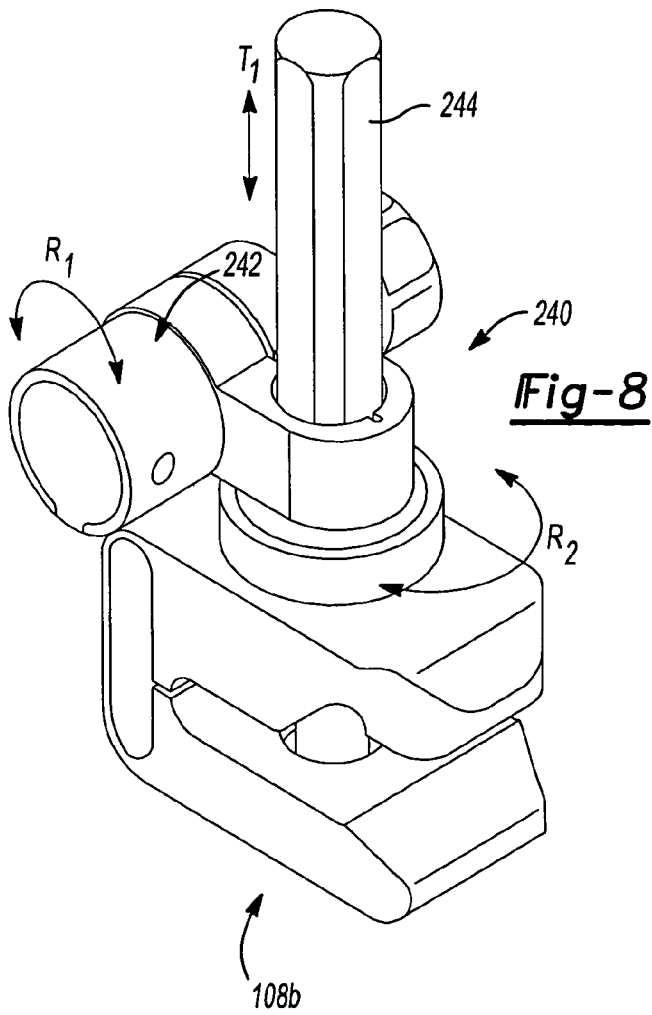
FIGS. 8, 8A, and 8B are perspective, side and plan views, respectively, of a clamping assembly according to the present teachings.
Figure 8A:
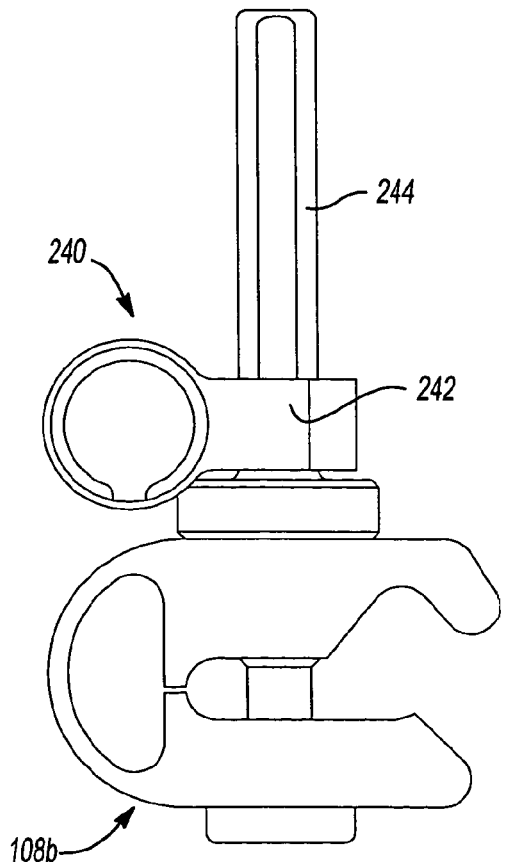
Figure 8B:
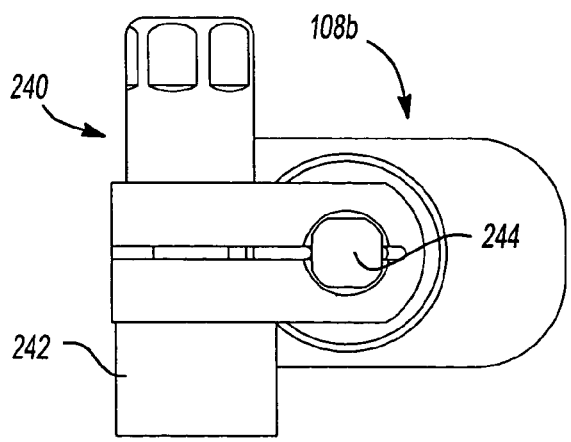
Figure 8C:
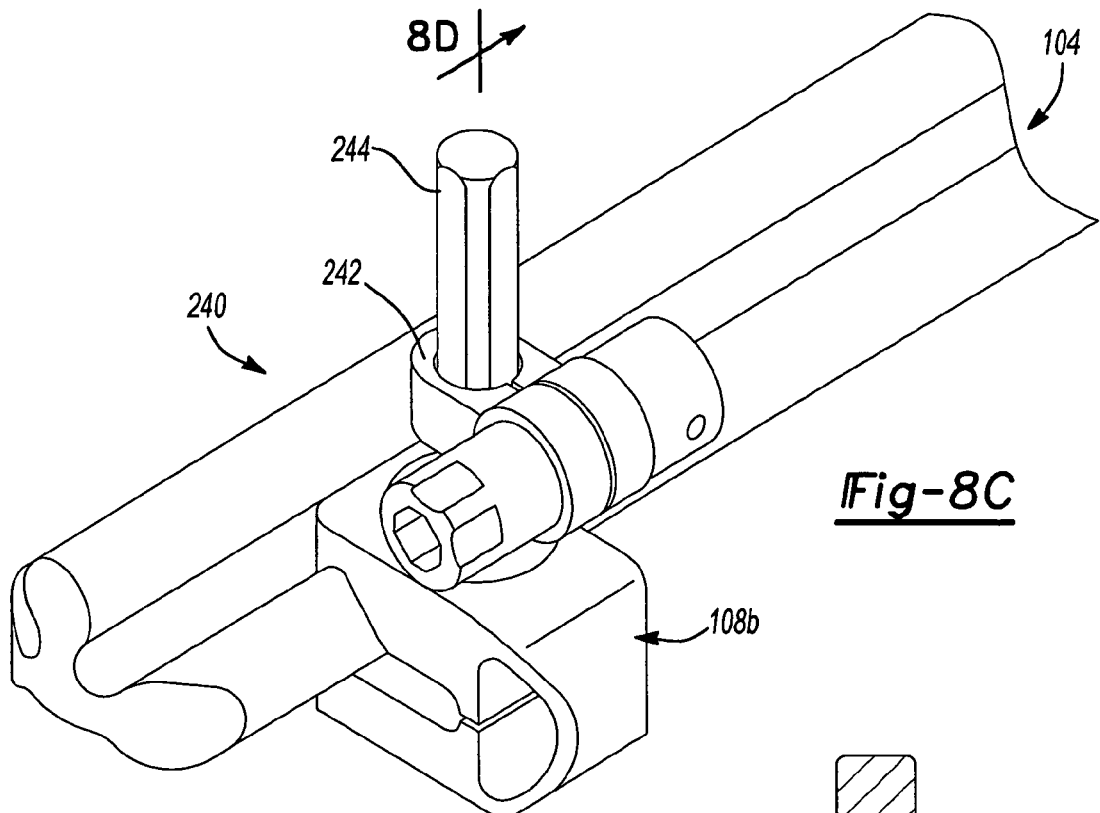
FIG. 8C is a perspective view of a detail of the clamping assembly of FIG. 8 shown coupled with a frame.
Figure 8D:
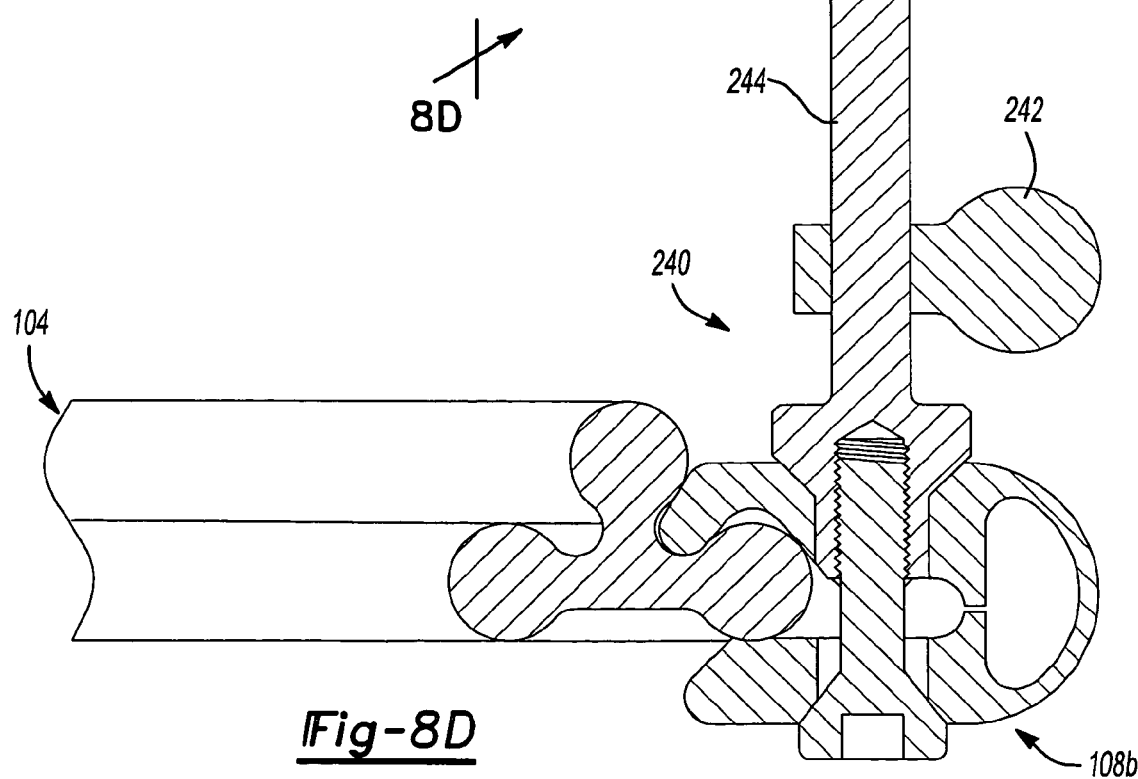
FIG. 8D is a sectional view of the detail shown in FIG. 8C.

Referring to FIGS. 8, and 8A-8D, an exemplary clamping assembly 240 configured for connecting one of the proximal and distal frames 102,104 with a fixation wire 110 (shown in FIG. 1) is illustrated. The clamping assembly 240 can include a translational/rotational coupler 242 and one snap-on frame clamp 108b rotatably coupled to a shaft 244. The shaft 244 is translationally coupled to the translational/rotational coupler 242. Referring to FIG. 8, adjustability in one translational direction, as indicated by bi-directional arrow $T_1$, and two mutually orthogonal rotational directions, as indicated by curved arrows $R_1$ and $R_2$, can be provided. Detailed views of the clamping assembly 240 at the connection with a distal frame 104 are illustrated in FIGS. 8C and 8D.

Referring to FIGS. 9, 9A, and 9B, a clamping assembly 240 configured for connecting one of the proximal and distal frames 102,104 with a rod, such a rod-shaped portion of one of the fixation components, is illustrated. The clamping assembly 240 can include a bi-rotational coupler 250 and one snap-on frame clamp 108b. The bi-rotational coupler 250 can include two rotationally coupled components 252, 254 for providing rotational adjustability about two orthogonal rotational directions, as indicated by curved arrows $R_2$ and $R_3$ in FIG. 9.

Figure 10:
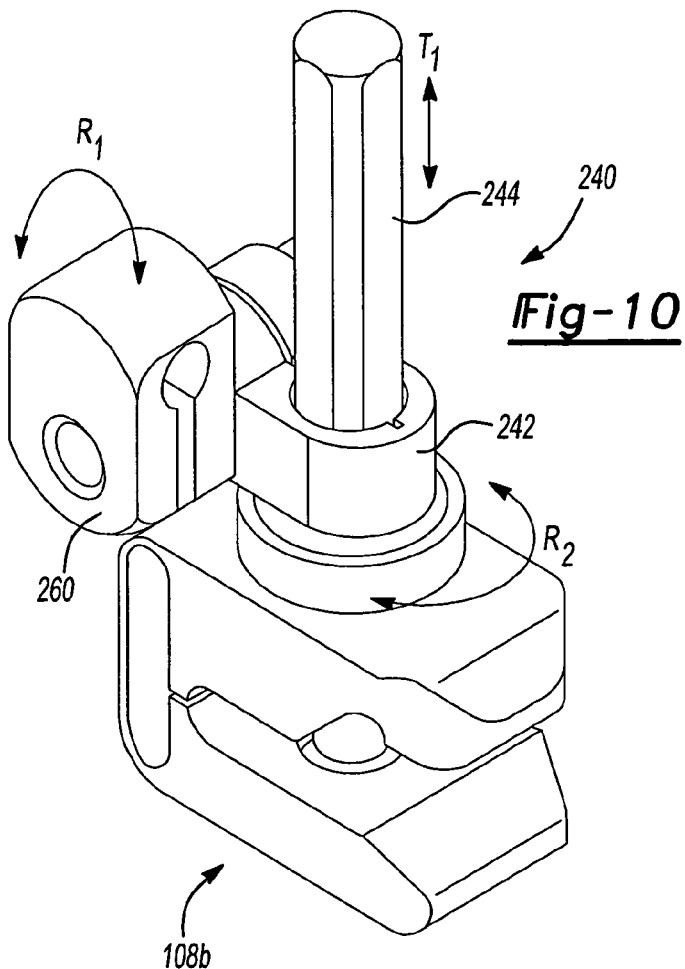
FIGS. 10, 10A, and 10B are perspective, side, and plan views, respectively, of a clamping assembly according to the present teachings.
Figure 10A:
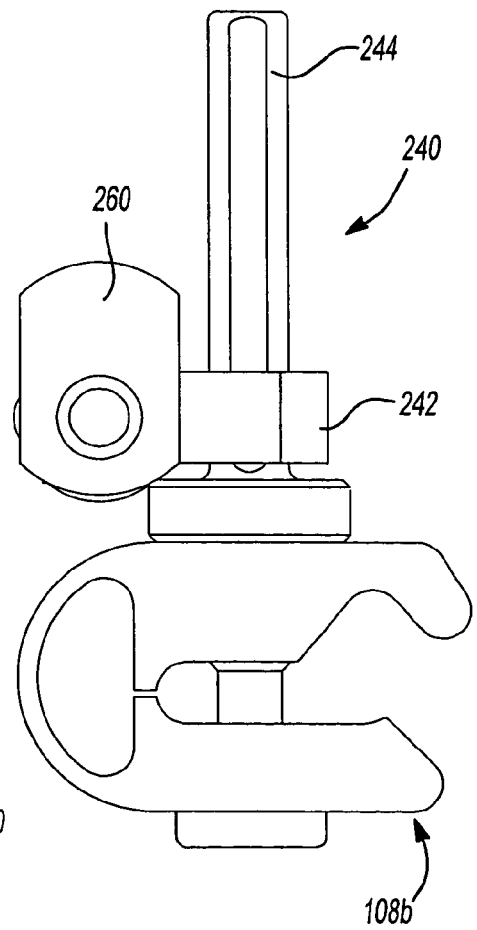
Figure 10B:
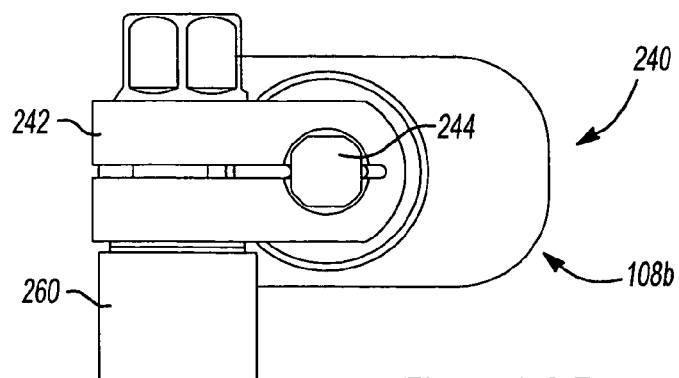

Referring to FIGS. 10, 10A, and 10B, a clamping assembly 240 configured for connecting one of the proximal and distal frames 102,104 with a bone screw is illustrated. The clamping assembly 240 can include one translational/rotational coupler 242 rotationally coupled to a bone screw clamp 260, and one snap-on frame clamp 108b having a shaft 244 translationally connected with the translational/rotational coupler 242. Referring to FIG. 10, he clamping assembly 240 can provide rotational adjustability about two orthogonal rotational directions, as indicated by curved arrows $R_2$ and $R_3$, and translational adjustability, as indicated by bi-directional b arrow $T_1$.

Referring to FIGS. 11, 11A, and 11B, a clamping assembly 240 configured for connecting one of the proximal and distal frames 102,104 with a fixation wire 110 and a frame connector 106 is illustrated. The clamping assembly 240 of FIG. 11 is similar to the clamping assembly 240 illustrated in FIG. 8, and includes the translational/rotational coupler 242, and the snap-on frame clamp 108b, which can be connected to the threaded portion 158 the frame connector 106, as shown, or to the contraction/distraction connector 106a of FIG. 5.

Referring to FIGS. 12, 12A, and 12B, a clamping assembly 240 configured for connecting one of the proximal and distal frames 102,104 with a bone screw and a frame connector 106 is illustrated. The clamping assembly 240 of FIG. 11 is similar to the clamping assembly 240 illustrated in FIG. 10, and includes the translational/rotational coupler 242, the bone screw clamp 260 and the snap-on frame clamp 108b, which can be connected to the threaded portion 158 the frame connector 106, as shown, or to the contraction/distraction connector 106a of FIG. 5.

Referring to FIGS. 13, 13A, and 13B, a clamping assembly 240 similar to the clamping assembly 240 of FIG. 11 is illustrated. The clamping assembly 240 of FIG. 13 includes additionally the bi-rotational coupler 250 coupling the frame clamp 108b and the frame connector 106.

Referring to FIGS. 14, 14A, and 14B, a clamping assembly 240 similar to the clamping assembly of FIG. 12 is illustrated.

The clamping assembly 240 of FIG. 14 includes additionally the bi-rotational coupler 250 coupling the frame clamp 108b and the frame connector 106.

From the above description it will be appreciated that the external fixation system 100 is a modular system that provides versatile fixation for many fracture/fusion conditions. A variety of radiolucent and/or radio-opaque components can be interconnected in various clamping assemblies 240 that enable translational and rotational adjustability about multiple independent directions. The components include, for example, proximal and distal frames 102, 104, various frame connectors 106, contraction/distraction connectors 106b, frame clamps 108b or other clamps 108, bi-rotational couplers 252, and translational/rotational couplers 242. The frames 102, 104 are configured to provide connection at any location along their continuous lobes 140. The frame connectors 106 can provide a selectable constant compressive force across the fracture/fusion site during non load-bearing use, and an automatically adjustable variable compressive force during load-bearing use, as directed by the surgeon.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. An external fixation system for a bone comprising:
 a proximal frame defining a continuous proximal boundary;
 a distal frame defining a continuous distal boundary, wherein at least one of the proximal frame or the distal frame comprises three separate and spaced apart continuous attachment surfaces oriented in a three-dimensional configuration and defining a tri-lobe frame cross section, each attachment surface defining an attachment lobe with a curved cross section, the attachment lobes arranged in a triangular configuration; and
 at least one frame connector configured for interconnecting the proximal and distal frames at any position along one of the attachment lobes of the at least one of the proximal frame or the distal frame, wherein the frame connector comprises a compliant mechanism for transmitting an adjustable compressible force to the bone, wherein the compliant mechanism is configured for transmitting a compressive force of constant magnitude to the bone during non load-bearing use, wherein the compliant mechanism comprises;
 first and second members telescopically and movable between a first position in which a gap therebetween is substantially closed and a second position in which the gap therebetween is open, the first connector member including a threaded portion, and an elongated slot defined on the threaded portion;
 a biasing member operable to transmit compression force when the gap is open;
 an activation knob rotatable for opening the gap and activating the biasing member; and
 a force-selector knob threadably connected to a threaded portion of the first connector member, the force-selector knob rotatable for engaging a pin, the pin transverse to the slot and movable along the slot for opening the gap.

2. The fixation system of claim 1, wherein the frame connector comprises a clamp configured for snap-on attachment at any position along one of the attachment lobes.

3. The fixation system of claim 1, wherein the compliant mechanism is further configured for automatically adjusting the magnitude of the compressive force to the bone during load-bearing use.

4. The fixation system of claim 1, wherein the frame connector comprises a mechanism for adjusting the magnitude of the compressive force to the bone.

5. The fixation system of claim 1, wherein the proximal and distal frames are radiographically translucent.

6. The fixation system of claim 1, wherein the frame connector is structurally configured for automatically adjusting the magnitude of the compressive force to the bone during load-bearing use.

7. The fixation system of claim 6, wherein the proximal and distal frames are radiographically translucent.

8. An external fixation system comprising:
   a proximal frame defining a continuous proximal boundary;
   a distal frame defining a continuous distal boundary; and
   at least one frame connector configured for interconnecting the proximal and distal frames at any position along at least one of the proximal and distal boundaries, wherein the frame connector includes a compliant mechanism configured for transmitting a compressive force of constant magnitude to the bone during non load-bearing use, and further configured for automatically adjusting the magnitude of the compressive force to the bone during load-bearing use, the compliant mechanism including:
      first and second members telescopically interconnected and defining a gap of variable opening therebetween, the first and second members movable between a first position in which the gap is substantially closed and a second position in which the gap is open, the first member including a threaded portion, an elongated slot defined in the threaded portion, and a pin transverse to the slot and movable along the slot;
      a biasing member coupled between the first and second members and operable to transmit a compression force when the gap is open;
      an activation knob threadably coupled to the second member and rotatable for opening the gap and activation the biasing member; and
      a force-selector knob threadably connected to the threaded portion of the first member, the force-selector knob rotatable for moving the pin along the slot and opening the gap.

9. The fixation member of claim 8, wherein the first member is cannulated and defines a longitudinal bore receiving the biasing member, and wherein the second member includes a sleeve receiving an unthreaded stem of the first member.

10. The fixation member of claim 9, further comprising:
    a bar attached to the sleeve of the second member, the bar having a threaded portion threadably engaged to the activation knob, the bar having a portion movably received in a bore of an extension member; and
    a set screw transversely inserted into the bore of the extension member and securing the bar relative to the extension member.

11. The fixation system of claim 8, wherein each frame comprises three continuous attachment surfaces in the form of curved attachment lobes substantially coextensive with the frame.

12. The fixation system of claim 11, further comprising at least one clamp assembly coupled to the frame connector and structurally configured for snap coupling onto any one of the attachment lobes.

13. The fixation system of claim 12, wherein the clamp assembly is at least partially radiographically translucent.

14. The fixation system of claim 12, wherein the clamp assembly further comprises a coupler adapted for rotational movement about two orthogonal axes.

15. The fixation system of claim 14, wherein the coupler is adapted for translational movement about at least one axis.

* * * * *

UNITED STATES PATENT AND TRADEMARK OFFICE
CERTIFICATE OF CORRECTION

PATENT NO.        : 7,422,593 B2                                    Page 1 of 1
APPLICATION NO.   : 11/297745
DATED             : September 9, 2008
INVENTOR(S)       : Jeffery Cresina et al.

It is certified that error appears in the above-identified patent and that said Letters Patent is hereby corrected as shown below:

Column 2
Line 39, after "bones" insert --.--.

Column 3
Line 25, "frame connector 108b" should be --frame connector 106--.

Column 4
Line 44, "108" should be --108b--.

Column 5
Line 37, "he" should be --the--.
Line 40, delete "b".
Line 49, after "158" insert --of--.
Line 58, after "158" insert --of--.

Column 6
Line 50, claim 1, ";" should be --:--.

Column 7
Line 30, claim 8, after "load-bearing use" insert --wherein the at least one of the
   proximal frame or the distal frame comprises three separate and spaced apart
   continuous attachment surfaces oriented in a three-dimensional configuration and
   defining a tri-lobe frame cross section, each attachment surface defining an
   attachment lobe with curved cross section, the attachment lobes arranged in
   triangular configuration, and wherein the frame connector is coupled to one of the
   attachment lobes,--.

Signed and Sealed this

Ninth Day of December, 2008

JON W. DUDAS
*Director of the United States Patent and Trademark Office*